(12) United States Patent
Roberts et al.

(10) Patent No.: US 10,939,850 B2
(45) Date of Patent: Mar. 9, 2021

(54) FOOT-BASED MOVEMENT MEASUREMENT

(71) Applicant: NURVV LIMITED, Twickenham (GB)

(72) Inventors: Jason Roberts, Twickenham (GB); Grant Trewartha, Calne (GB); Geoffrey Noonan, Woking (GB); Giles Tongue, West Byfleet (GB)

(73) Assignee: NURVV LIMITED, Twickenham (GB)

(*) Notice: Subject to any disclaimer, the term of this patent is extended or adjusted under 35 U.S.C. 154(b) by 198 days.

(21) Appl. No.: 16/239,266

(22) Filed: Jan. 3, 2019

(65) Prior Publication Data
US 2020/0214596 A1    Jul. 9, 2020

(51) Int. Cl.
*A61B 5/103* (2006.01)
*A61B 5/00* (2006.01)

(52) U.S. Cl.
CPC .......... *A61B 5/1038* (2013.01); *A61B 5/6807* (2013.01); *A61B 5/7203* (2013.01); *A61B 2560/0475* (2013.01); *A61B 2562/0247* (2013.01); *A61B 2562/046* (2013.01)

(58) Field of Classification Search
CPC ... A61B 5/1038; A61B 5/6807; A61B 5/7203; A61B 2560/0475; A61B 2562/0247; A61B 2562/046
See application file for complete search history.

(56) References Cited

U.S. PATENT DOCUMENTS

2014/0200486 A1*  7/2014  Bechtel .................. A61B 5/447
                                                              600/592

FOREIGN PATENT DOCUMENTS

GB          2549513 A      10/2017

OTHER PUBLICATIONS

Garcia-Pinillos, F., et al. "Absolute Reliability and Concurrent Validity of the Stryd System for the Assessment of Running Stride Kinematics at Different Velocities." Journal of Strength and Conditioning Research (May 2018) pp. 1-7.

* cited by examiner

*Primary Examiner* — Peter J. Macchiarolo
*Assistant Examiner* — Anthony W Megna Fuentes
(74) *Attorney, Agent, or Firm* — Stites & Harbison, PLLC; Jeffrey A. Haeberlin; Gary N. Stewart (57) ABSTRACT

A method and system for calibrating a measurement from a shoe-based sensor device for measuring pressure at one or more parts of a shoe sole and providing at least one pressure sensor measurement signal indicating the measured pressure, the method being performed at a processor that receives the at least one pressure sensor measurement signal and including: determining a minimum value for the at least one pressure sensor measurement signal and storing the determined minimum value as a correction constant in a data memory associated with the processor; and correcting a value for the at least one pressure sensor measurement signal received subsequent to the step of storing, by the stored correction constant.

12 Claims, 5 Drawing Sheets

FOOT-BASED MOVEMENT MEASUREMENT

TECHNICAL FIELD OF THE DISCLOSURE

The disclosure relates to measuring at least one metric associated with foot-based movement, measuring a metric characterising a health of a subject's running behaviour and calibrating a measurement from a shoe-based sensor device and corresponding foot-based data metric system or systems.

Background to the Disclosure Tracker devices which are inserted in a shoe and which provide a limited amount of information on the distance and pace of a run or walk are known. GB-2549513, commonly owned with the present application, describes such an insole (or inner sole) and a system comprising the insole together with a remote device to receive information from a transmitter of the insole. The insole has two pressure sensors: one positioned in the heel region; and a second positioned in a forefront region. Data indicating optimum footwear use for a user, for instance how a user's weight is distributed as their foot lands on the ground and/or how much pressure they are putting on their feet when moving from side to side; may be measured. It is suggested that information on their gait, footstrike and/or player loading could be identified accordingly in real time.

Metrics are also known for measuring the running behaviour of a subject (a person), to identify whether their running technique is healthy and/or sustainable. Known metrics include: ground Contact Time, which is the average length of time the foot spends in contact with the ground during each step; running "power", which is an attempted surrogate measurement of metabolic power (that is, calories burned); and a "running index", which is a combination of heart rate and running speed data to give a health score. "Absolute Reliability and Concurrent Validity of the Stryd System for the Assessment of Running Stride Kinematics at Different Velocities", Garcia-Pinillos et al, Journal of Strength and Conditioning Research, May 2018 discusses a number of such measurements in terms of their absolute reliability, noting room for improvement. Such measurements are typically determined using accelerometer measurements. These may affect the quality of the metrics calculated. For example, the data may need a significant amount of processing to be interpreted properly. Also, existing systems have used accelerometers with limited dynamic range and sampling rate.

Improving such systems to measure these and other characteristics dynamically, more accurately and/or more efficiently is therefore desirable.

SUMMARY OF THE INVENTION

Against this background and in a first aspect, there is provided a method for measuring at least one metric associated with foot-based movement. A second aspect provides a method for measuring a metric characterising a health of a subject's running behaviour. In a third aspect, there is provided a method for calibrating a measurement from a shoe-based sensor device. In accordance with either or both aspects, there may be considered a corresponding foot-based data metric system. The foot-based data metric system may be configured to perform the method or methods.

At least one metric associated with foot-based movement may be measured based on a combination of at least three pressure sensor measurement signals, for instance from respective sensors in a shoe or insole. Each pressure sensor measurement signal indicates a respective pressure measurement taken at a respective, different part of the foot (that is, a different place on the sole of the foot) during movement (such as during walking, running, jumping, hopping). The metrics measured may include: footstrike; pronation; cadence; and step length. More than one metric may be measured, especially simultaneously. The procedure may be performed (in the same way or in different ways) for multiple feet, to determine the same or different metrics. Footstrike can be measured by determining a time of rear-foot contact and a time of mid-foot contact and comparing the determined times of the determined time of rear-foot contact and the determined time of mid-foot contact, in particular identifying a difference between the two times. The footstrike can then be classified based on the difference, for example by comparing it with one or more than one timing threshold. The time or times of contact may be a time at which the respective pressure sensor measurement signal or signals is or are at least a signal threshold value. The signal threshold value for rear-foot contact is preferably the same as the signal threshold value for mid-foot contact, but they may be different. Multiple pressure sensor signals are advantageously combined (for instance, a linear combination such as a sum or weighted sum) to determine one or both of the times of contact.

Measuring pronation by determining medial and lateral pressure levels and, in particular, establishing a ratio of the pressure levels is additionally or alternatively possible. The pronation can then be classified based on the ratio, for example by comparing it with one or more than one pronation threshold. Multiple pressure sensor signals are advantageously combined (for instance, a linear combination such as a sum or weighted sum) to determine one or both of pressure levels. A time at which the foot initially contacts a ground may be identified, such that the pressure level may be based on pressure measurement a predetermined time duration subsequently.

A metric characterising a health of a subject's running behaviour can use first and second foot-based sensor devices (such as in a shoe or insole), each device including pressure sensors for measuring pressure at a different part of the respective foot and providing pressure sensor measurement signals indicating the measured pressure. The metric can be computed by a processor based on the received pressure sensor measurement signals. At least one metric associated with foot-based movement (for example, one or more of: footstrike; pronation; cadence; and step length, as noted above) is measured for each foot, based on a combination of the pressure sensor measurement signals received from the respective foot-based sensor device (the same metric or metrics being measured for the two feet). By evaluating the metric or metrics for feet against one another, an asymmetry level is established (for each metric), which can be used to determine the metric characterising the health of a subject's running behaviour. Preferably, multiple such asymmetry levels are thereby determined.

Each asymmetry level with may be compared with at least one level threshold, to classify the respective asymmetry level and the classification may then be used to determine the metric characterising the health of a subject's running behaviour. For example, the classification could be a number. Then, the metric characterising the health of a subject's running behaviour can be based on a combination (for example, a sum or a linear, arithmetic or weighted combination) of the classification numbers.

The metric characterising the health of a subject's running behaviour can also be based on other metrics for the subject, such as one or more of: acute to chronic workload ratio; a cadence (for each foot); and a pronation metric (for each foot). Each of these may also be classified by comparison with one or more respective thresholds, for example to provide a number. The metric characterising the health of a subject's running behaviour may then be based on a combination (for example, a sum or a linear, arithmetic or weighted combination) of the classification numbers. The weight for the classification for acute to chronic workload ratio is preferably higher than the weight for each asymmetry level classifications and/or for cadence or pronation.

A shoe-based sensor device may be used for measuring pressure at one or more parts of a shoe sole and providing a pressure sensor measurement signal (or signals) indicating the measured pressure. Calibrating a measurement from the shoe-based sensor may be achieved by determining a minimum value for each pressure sensor measurement signal and storing each determined minimum value as a respective correction constant. A subsequently-received value for each pressure sensor measurement signal may be corrected by the stored respective correction constant. Preferably multiple pressure sensor measurement signals are corrected, each by means of a respective correction constant based on the minimum value. Each minimum value is advantageously determined from multiple samples of the respective pressure sensor measurement signal taken over a time duration.

The time duration could be based on a time period in which the shoe is undergoing movement. The samples for determining the minimum value (or values) may be collected, over a time duration within the time period in which movement of the shoe is identified. This time period could be in which the shoe takes a predetermined number of steps, in particular at least two or more preferably at least five. This process may be repeated at (regular) time intervals.

Additionally or alternatively, the time duration may be set based on receipt of a signal at the processor (for instance, from a user of the system) indicating that no load is being applied to the shoe. Then, the samples for determining the minimum value (or values) may be collected over a time duration having a start set in response to receiving the signal. The time duration may have a predetermined length, for example at least 20 seconds and/or no more than one minute.

For any aspect of the disclosure, a foot-based data metric system may be considered, comprising: at least one foot-based sensor device, each device including a plurality of pressure sensors configured to measure pressure at a different part of the respective foot and providing one or more pressure sensor measurement signals indicating the measured pressure; and a processor, configured to receive the one or more pressure sensor measurement signals from the at least one foot-based sensor device and to perform the method of any preceding claim. Each foot-based sensor device advantageously comprises a shoe insole, in which the plurality of pressure sensors are provided. The pressure sensors may each comprise a respective force-sensitive resistor.

DETAILED DESCRIPTION OF PREFERRED EMBODIMENTS

The present disclosure relates to measuring foot-based metrics based on pressure measurements taken at different parts of the foot. In particular, the pressure measurements are taken using shoe-based sensors, which may be provided in a shoe or as part of an insole (inner sole). The determination of basic, step-based metrics will be discussed first. Then, the establishment of more complex metrics, particularly concerning running behaviour will then be presented. Field calibration of the sensors will be explained next. Finally, further fitness-based metrics will be detailed.

In general terms, it will be understood that there is disclosed a foot-based or shoe-based data metric system, comprising at least one foot-based or shoe-based sensor device (such as an insole or shoe part or component), each device including a plurality of pressure sensors (which may be mounted on or embedded in the device), each of which is configured to measure pressure at a different part of the respective foot or shoe (particularly an underfoot or sole part). The sensor device is further configured to provide one or more pressure sensor measurement signals, each of which indicates the measured pressure of a respective sensor. The system further includes a processor, configured to receive the one or more pressure sensor measurement signals from the at least one foot-based or shoe-based sensor device and to perform a method or technique of data collection, measurement, calibration and/or operation, as disclosed herein. The system may be configured to perform one or more such method or technique. Techniques and/or aspects of the system will be discussed below in both generalised and specific terms.

Step-Based Metrics

As noted above, pressure measurements are taken using foot-based or shoe-based sensors, particularly in the form of insoles. GB-2549513 (noted above) discusses one design of such insoles. A more sophisticated design may be used, in which the insoles comprise embedded pressure sensors, in the form of Force Sensitive Resistors (FSR) to record the pressure distribution patterns occurring across the bottom surface (sole) of the foot, particularly during running ground contacts. Multiple such sensors are provided, with a minimum of 2 sensors per foot, but preferably at least 3 or 5. In practice, 16 FSRs are provided per insole.

Figure 1:
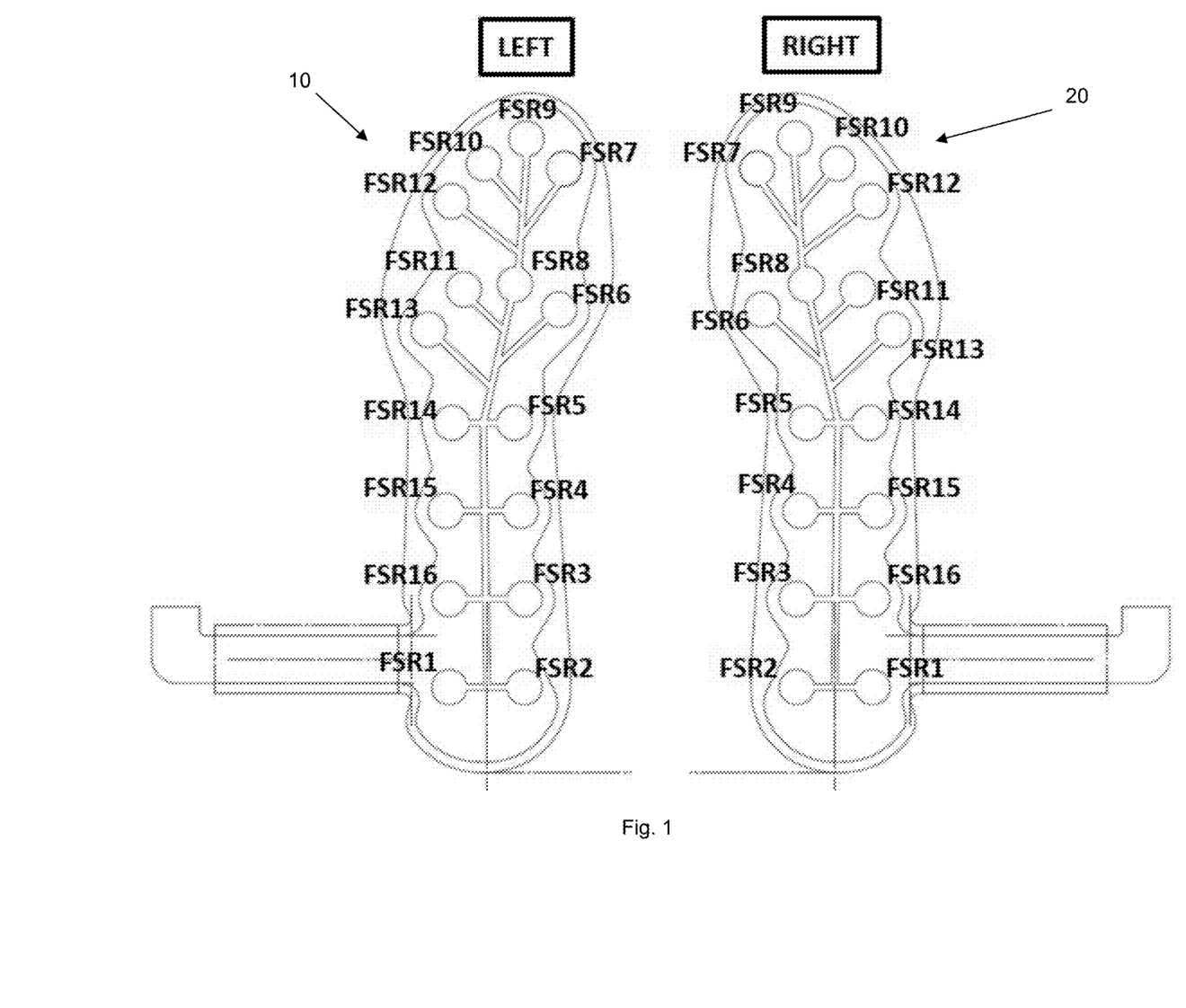
FIG. 1 shows a schematic diagram of sensor patterns for measuring pressures in feet.

With reference to FIG. 1, there is shown a schematic diagram of sensor patterns for measuring pressures in feet. The placement of the FSRs (numbered 1 to 16) on each of the left insole 10 and the right insole 20 are shown. The output of the FSRs is used as the basis for computing a number of metrics associated with running technique and/or form. In order to calculate these metrics, the output signals from the FSRs are provided to a processor, which also may be embedded in the insole, provided in a shoe, located in an item also positioned on a subject's body, for example a smart-watch or smartphone or located remotely from the subject (for example, a server). Suitable communication interfaces may be connected to the FSRs to allow the information in their output signals to be communicated to the processors.

The metrics that may be computed by include cadence, pronation, footstrike, step length (which may be computed based on pressure measurements alone or combined with other data streams). Raw signals from each FSR are acquired at 1000 samples per second and these data streams are conditioned and combined in various ways to calculate the required outcome metrics.

The algorithms used to determine these measures, as will be discussed below have been customised and/or optimised for use with pressure measurement signals. As noted above, existing techniques aiming to calculate the same metrics have used different sensor types, mainly accelerometers. In particular, it has been found that sophisticated metrics can be determined using a combination of three or more pressure sensor measurements.

The benefit of these metric calculations is that they can be delivered in real-time during running sessions via visual or audio cues (if the user selects these options), to allow the user to attempt to make corrections within a session. A comprehensive dataset coming from the pressure sensors may be reduced to a set of categories which the user can understand and attempt to make changes in technique against.

In general terms, there may therefore be considered a method for measuring at least one metric associated with foot-based movement. The method comprises: receiving at a processor, at least three pressure sensor measurement signals for a foot, each pressure sensor measurement signal indicating one or more pressure measurements taken at a respective, different part (places on the sole) of the foot during movement; and computing, at the processor, the at least one metric associated with foot-based movement based on a combination of the received at least three pressure sensor measurement signals from the foot. The at least one metric associated with foot-based movement characterises one or more of: footstrike; pronation; cadence; and step length.

The procedure may be applied to more than one foot. For example, the foot may be a first foot of a subject and the subject may have a second foot. Then, at least three pressure sensor measurement signals for the second foot may be received at the processor. Each pressure sensor measurement signal may indicate one or more pressure measurements taken at a respective, different part of the second foot during the movement (which is the same movement of the subject as for the first foot). Then, the step of computing is further based on a combination of the received at least three pressure sensor measurement signals from the second foot. The computing steps for the second foot may be the same as for the first foot, although there may be differences (for example, in respect of specific parameters). The step of computing may comprise: computing, at the processor, the at least one metric associated with foot-based movement based on a combination of the received at least three pressure sensor measurement signals from the first foot; and computing, at the processor, the at least one metric associated with foot-based movement based on a combination of the received at least three pressure sensor measurement signals from the second foot. Advantageously, the at least one metric computed for the first foot and the at least one metric computed for the second foot characterise the same feature or features.

Further generalised features of the disclosure will be noted below, but more information about the specific implementation will first be provided.

A first metric that may be computed is footstrike. Footstrike refers to the part of the foot which makes initial contact with the ground during each running step. It is linked to running performance and potentially injury risk. Footstrike is normally classified into 3 sub-categories: rearfoot strike, midfoot strike, forefoot strike.

The calculation method involves grouping individual FSRs into 'zones'. Specifically, the sensors are grouped into at least two zones: a rear-foot (heel) zone; and a mid-foot zone. Then, the signals from the respective sensors in each zone are combined, specifically summed. The combined signal is then used to determine, for each foot, a time at which that zone of the foot has made contact with the ground (desirably, to the nearest 1 millisecond, ms). This is identified based on the combined signal exceeding a threshold. The time difference between the rear-foot zone time of initial contact and "mid-foot" zone time of initial contact is used as the basis for categorising the foot contact as rearfoot, midfoot, or forefoot.

An algorithmic description of the procedure is now set out.

For each foot:
Rear_Zone=sum(FSR1,2,3,16) [group of 4 "heel" sensors]
Mid_Zone=sum(FSR5,6,8,11,13,14) [group of 6 "midfoot" sensors]
Time of Rearfoot Contact=Rear_Zone>40000 units
Time of Midfoot Contact=Mid_Zone>40000 units A footstrike classification based on the relative timing between Rearfoot Contact and Midfoot Contact is then identified:
forefoot strike=if Time of Midfoot Contact is less than 10 ms later than Time of Rearfoot Contact
midfoot strike=if Time of Midfoot Contact is between 10 ms and 42 ms later than Time of Rearfoot Contact
rearfoot strike=if Time of Midfoot Contact is greater than 42 ms later than Time of
Rearfoot Contact The values used for establishing the time of Rearfoot Contact and/or the time of Midfoot Contact (both 40000 units in this case, although in practice, these could be different from one another) are threshold values and are not necessarily fixed. They may be adjusted based on other measurements, for example dynamically. In particular, adjustments to these thresholds may be made following field calibration of the sensors, as discussed below. This technique may also (or alternatively) be used for determining step count, for example by comparing the sum of sensor measurements from sensors over the whole foot (which may be all of the sensors or a subset of sensors across the foot) against a threshold.

Returning to the general terms noted previously, a metric of the at least one metric associated with foot-based movement may characterise footstrike. Then, the step of computing preferably comprises: determining a time of rear-foot contact, based on one or more of the received pressure sensor measurement signals indicating a pressure measurement taken at a rear part of the foot; and determining a time of mid-foot contact, based on one or more of the received pressure sensor measurement signals indicating a pressure measurement taken at a middle part of the foot. A metric characterising footstrike may be established based on a comparison of the determined time of rear-foot contact and the determined time of mid-foot contact, particularly based on a difference of the determined time of rear-foot contact and the determined time of mid-foot contact.

The steps of determining times of contact may comprise determining a time at which the one or more of the received pressure sensor measurement signals is at least a signal threshold value. For example, the time of rear-foot contact may be determined by determining a time at which the one or more of the received pressure sensor measurement signals indicating a pressure measurement taken at a rear part of the foot (in particular, a combination of multiple signals, such as a linear combination, sum or weighted sum) is at least a first signal threshold value. Additionally or alternatively, a time of mid-foot contact may be determined by determining a time at which the one or more of the received pressure sensor measurement signals indicating a pressure measurement taken at a middle part of the foot (in particular, a combination of multiple signals, such as a linear combination, sum or weighted sum) is at least a second signal threshold value. Typically, the first signal threshold value and the second signal threshold value are the same. The first signal threshold and/or the second signal threshold may be predetermined or varied dynamically during use, for example based on iterative feedback or calibration (as will be discussed below). In general, both the time of rear-foot contact and the time of mid-foot contact are based on multiple received pressure sensor measurement signals, but it may be possible for one time measurement to be based on a single received pressure sensor measurement signal.

The step of establishing preferably comprises comparing a difference between the determined time of rear-foot contact and the determined time of mid-foot contact with at least one timing threshold. Then, the footstrike may be classified based on the step of comparing. Advantageously, the classification is the metric characterising footstrike. More preferably, the at least one timing threshold comprises first and second timing thresholds. Then, a first classification (such as, forefoot strike) may be applied if the difference is less than the first timing threshold, a second classification (for example, midfoot strike) may be applied if the difference is greater than the first timing threshold and less than the second timing threshold and a third classification (rearfoot strike, for instance) may be applied if the difference is greater than the second timing threshold. The first timing threshold is set typically between 5 and 20 ms. The second timing threshold may be between 30 and 50 ms. The first timing threshold and/or the second timing threshold may be predetermined or varied dynamically during use, for example based on iterative feedback.

A second metric that may be computed is pronation. Pronation is a complex motion of the foot during walking and running, involving rotational movements about 3 joints: eversion of the subtalar joint, dorsiflexion of the ankle joint and abduction of the forefoot. Pronation occurs naturally during the first half of a stance phase during running and is a primary way of the body absorbing the energy of the impact within the ground.

A degree of pronation during running steps is considered healthy ("neutral pronation"). However, excessive pronation ("over pronation"), or restricted pronation ("under pronation") is considered unhealthy and considered to increase injury risk for runners.

Pronation is a motion of the foot relative to the lower leg, but its effect is reflected in the balance of foot pressure underneath the medial (inside) and lateral (outside) regions of the foot. Neutral pronation has a balance medial-lateral pressure, over pronation has more medial pressure than lateral pressure, under pronation has more lateral pressure than medial pressure. Therefore, it has been found that a pronation metric can be determined by calculating the average medial-lateral balance in pressure during the initial stance period for each running step contact. Thresholds can be used to classify each step into 3 sub-categories: neutral pronation, over pronation, or under pronation.

An algorithmic description of the procedure is now set out. The procedure for the left foot is as follows.

For each ground contact of the left foot:
From StepLeft (the initial time of left foot ground contact) to StepLeft+0.100 seconds (calculated for each time stamp available):
  MedialPressure(Left)=(FSR2+FSR3+FSR4+FSR5+FSR6+FSR8)
  LateralPressure(Left)=(FSR1+FSR16+FSR15+FSR14+FSR13+FSR11)
  PronationRatio(Left)=MedialPressure(Left)/LateralPressure(Left)
  Pronation(Left)=average(PronationRatio(Left)) [over the 100 samples
  If Pronation(Left) is <=0.60, then Pronation(Left)=under-pronation (UP)
  If Pronation(Left) is 0.61 to 1.20, then Pronation(Left)=neutral-pronation (NP)
  If Pronation(Left) is >=1.21, then Pronation(Left)=over-pronation (OP)

For each ground contact of the right foot:
From StepRight (the initial time of left foot ground contact) to StepRight+0.100 seconds (calculated for each time stamp available):
  MedialPressure(Right)=(FSR2+FSR3+FSR4+FSR5+FSR6+FSR8
  LateralPressure(Right)=(FSR1+FSR16+FSR15+FSR14+FSR13+FSR11)
  PronationRatio(Right)=MedialPressure(Right)/LateralPressure(Right)
  Pronation(Right)=average(PronationRatio(Right)) [over the 100 samples]
  If Pronation(Right) is <=0.60, then Pronation(Right)=under-pronation (UP)
  If Pronation(Right) is 0.61 to 1.20, then Pronation(Right)=neutral-pronation (NP)
  If Pronation(Right) is >=1.21, then Pronation(Right)=over-pronation (OP)

When determined the MedialPressure and/or Lateral Pressure for a specific foot, the summed sensor outputs may be adjusted by a correction factor. For example, the correction factor may be set following field calibration of the sensors, as discussed below. The correction factor may be set on initial configuration or calibration and/or adjusted dynamically following 'in-run' calibration.

With reference to the general terms discussed previously, a metric of the at least one metric associated with foot-based movement may characterise pronation. Then, the step of computing preferably comprises: determining a medial pressure level, based on one or more of the received pressure sensor measurement signals indicating a pressure measurement taken at a first side of the foot; and determining a lateral pressure level, based on one or more of the received pressure sensor measurement signals indicating a pressure measurement taken at a second side of the foot opposite the first side. Then, a metric characterising pronation may be established based on a ratio of the determined medial pressure level and the determined lateral pressure level.

Each pressure level is optionally based on a combination (for instance, linear combination, sum or weighted sum) of a plurality of the received pressure sensor measurement signals. In other words, the medial pressure level may be based on a combination of a plurality of the received pressure sensor measurement signals, each of which indicate a pressure measurement taken at the first side of the foot and/or the lateral pressure level may be based a combination of a plurality of the received pressure sensor measurement signals, each of which indicate a pressure measurement taken at the second side of the foot.

One or more of the received pressure sensor measurement signals may be used to identify a time at which the foot initially contacts a ground. Then, each of the pressure levels is preferably based on the respective one or more of the received pressure sensor measurement signals for a (predetermined) time duration from the identified time at which the foot initially contacts the ground. For instance, the medial pressure level may be based on the one or more of the received pressure sensor measurement signals indicating a pressure measurement taken at a first side of the foot for a (predetermined) time duration from the identified time at which the foot initially contacts the ground. Additionally or alternatively, the lateral pressure level may be based on the one or more of the received pressure sensor measurement signals indicating a pressure measurement taken at a second side of the foot for a (predetermined) time duration from the identified time at which the foot initially contacts the ground. The (predetermined) time duration for the medial pressure level is normally the same as the (predetermined) time duration for the lateral pressure level, but they could be different. A (predetermined) time duration of between 0.05 and 0.2 seconds is typical and 0.1 seconds preferred.

A plurality of ratios of the determined medial pressure level and the determined lateral pressure level may be determined over the predetermined time duration. The metric characterising pronation may be established based on a combination of the plurality of determined ratios, for example an average (preferably a mean, but optionally a median or a mode).

The determined ratio of the determined medial pressure level and the determined lateral pressure level (which may be derived from the combination of ratios, if a plurality of ratios are used) may be compared with at least pronation threshold. Then, the pronation is beneficially classified based on the step of comparing. In this case, the classification may be the metric characterising pronation. More preferably, the at least one pronation threshold comprises first and second pronation thresholds. Then, a first classification (under-pronation) may be applied if the ratio is less than the first pronation threshold. A second classification (neutral-pronation) may be applied if the ratio is greater than the first pronation threshold and less than the second pronation threshold. A third classification (over-pronation) may be applied if the ratio is greater than the second pronation threshold. The first pronation threshold is set typically between 0.5 and 0.75. The second pronation threshold (higher than the first pronation threshold) may be between 0.5 and 1.5. The first pronation threshold and/or the second pronation threshold may be predetermined or varied dynamically during use, for example based on iterative feedback.

Running Behaviour Metrics

Although step-based metrics can be useful, it is desirable to determine a further measurement indicative of a healthiness and/or sustainability of a subject's running behaviour. It may thereby allow the subject (user) to reduce risk factors which could contribute to an elevated risk of injury. This indicative measurement is based a combination of a plurality of measurements, for instance including the step-based metrics detailed above.

This overall indicative measurement has been termed "Running Health" and is intended to take the form of a score within the range 0-100. A higher assigned score is associated with better running: a score of "100" represents optimal running; a score of "0" is running in such a manner which will maximise the risk of injury.

Running Health may be assessed over a number of different time periods: a score may be generated against an individual run, or multiple scores from several runs may be averaged together to give a score representing the user's average running health across a given period of time.

Figure 2:
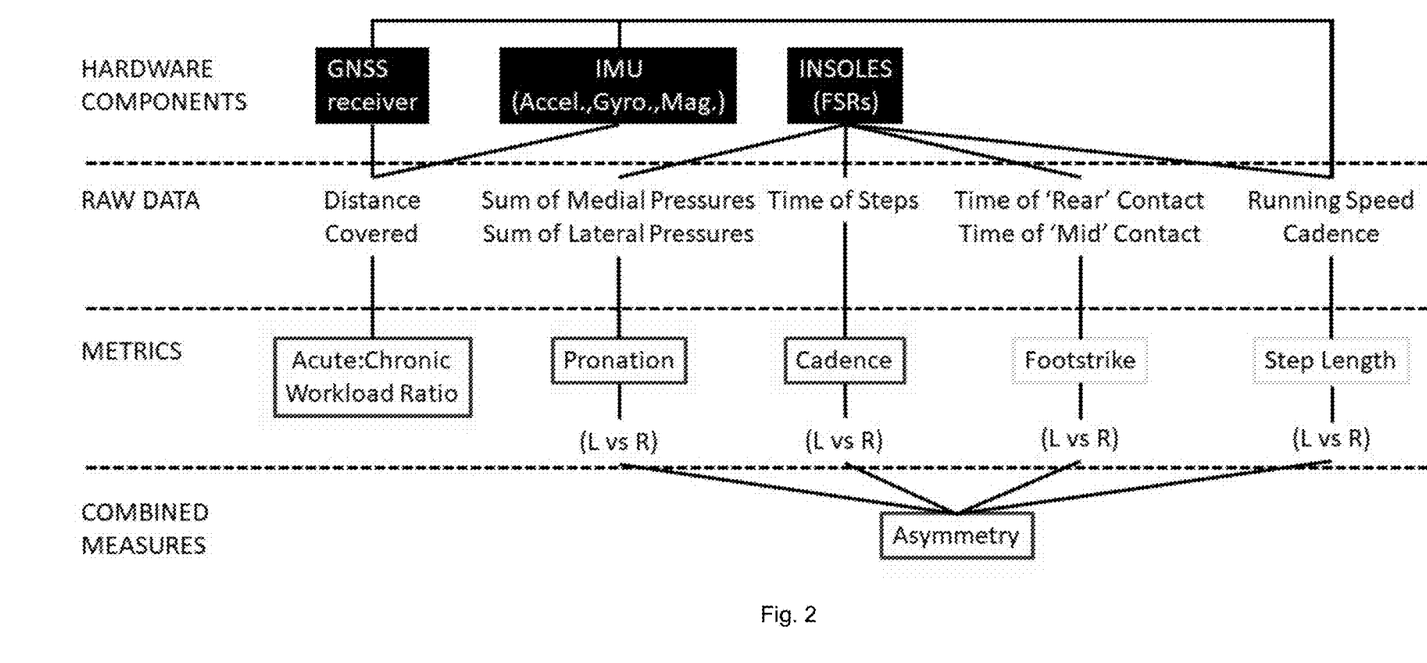
FIG. 2 illustrates a general approach for determining a running behaviour metric.

Referring to FIG. 2, there is illustrated a general approach for determining such a running behaviour metric. As will be seen from this drawing and as noted above, Running Health is calculated using several factors. Most of these factors may be determined from shoe-based or foot-based pressure sensors as discussed above. However, others may be determined using other measurement technologies (for example, an accelerometer and/or location information from a Global Navigation Satellite System or GNSS), which in some cases, may be combined with measurements provided by the shoe-based or foot-based pressure sensors. In any event, determining the metrics typically involves identifying intermediate measurements (labelled "Raw Data" in the drawing).

Individual metrics and/or combined measures included in Running Health score are based on established evidence linking the metric to either injury risk or running efficiency (economy) in runners. This will be discussed further below, with reference to particular metrics used.

In a number of cases, determining a metric for multiple feet (left and right) can be used to identify a level of asymmetry. The level of asymmetry (specifically for each metric, but optionally as a combined asymmetry metric) may then be used as a factor for determining Running Health. Other factors may also be combined with the one or more levels of asymmetry, for example as a weighted sum.

In practice, each factor is classified according to its value on a scale. In other words, a numerical classification is allocated based on the determined metric. The scale for a factor in Running Health assigns values between 0 (poor) and 5 (excellent). Running Health is then based on a combination (specifically, a weighted sum) of the values assigned for each factor.

In general terms, there may be considered as an aspect, a method for measuring a metric characterising a health of a subject's running behaviour. The method uses a system comprising: first and second foot-based sensor devices, each device including a plurality of pressure sensors for measuring pressure at a different part of the respective foot and providing pressure sensor measurement signals indicating the measured pressure; and a processor, configured to receive the pressure sensor measurement signals from the first and second foot-based sensor devices. At the processor: a metric associated with foot-based movement is measured based on a combination of pressure sensor measurement signals received from the first foot-based sensor device, in respect of a first foot of the subject; and a metric associated with foot-based movement is measured based on a combination of pressure sensor measurement signals received from the second foot-based sensor device, in respect of a second, different foot of the subject. The metric computed for the first foot and the metric computed for the second foot characterise the same feature. The metric measured for the first foot is evaluated against the metric measured for the second foot to identify an asymmetry level. Then, the metric characterising the health of a subject's running behaviour is based on the identified asymmetry level. In practice, multiple metrics may be determined for each foot and then, multiple asymmetry levels may be determined by evaluating each metric measured for the first foot against the metric measured for the second foot characterising the same feature. The metric characterising the health of a subject's running behaviour may then be based on the identified asymmetry levels (for example a combination of the identified asymmetry levels).

The metric or metrics computed for the first and/or second foot may include for instance, one or more of: footstrike; pronation; cadence; and step length. The metric may be determined in accordance with any method or system disclosed herein, especially for footstrike and/or pronation. Each asymmetry level may be determined based on a ratio (for instance, represented as a percentage) of the respective metric determined for the first foot (for instance, left) against the respective metric determined for the second foot (right, although the left and right designations could be swapped). In some embodiments, the asymmetry level may be determined by evaluating whether or not the respective metric determined for the first foot is the same as the respective metric determined for the second foot. Each asymmetry level may be determined for a single step and an overall asymmetry level may be determined for multiple steps based on a combination of the asymmetry level determined for each step (such as an average, sum or weighted sum or, where the asymmetry level per step is binary, that is symmetric or asymmetric, as a ratio of asymmetric steps to total steps). Additionally or alternatively, an asymmetry level may be determined based on a comparison of a combination of the respective metrics for each step of the first foot and a combination of the respective metrics for each step of the second foot. The combinations may be a sum or weighted sum or average, for instance.

Preferably, each asymmetry level is compared with a respective level threshold or respective level thresholds. Then, each asymmetry level may be classified based on the step of comparing. The metric characterising the health of a subject's running behaviour may thereby be based on the classification. In particular, the classification may be a number (for example, on a scale from zero to a predetermined maximum value, such as 5). In that case, the metric characterising the health of a subject's running behaviour is preferably based on a combination (such as a linear combination, arithmetic combination, sum or weighted sum) of the identified plurality of classifications (that is, numbers). In addition to one or more asymmetry levels, the metric characterising the health of a subject's running behaviour may additionally be based on one or more specific metrics computed for the first and/or second foot, for instance as identified above and/or one or more further metrics. Further details of this generalised description will be discussed below, but more specific details on the parameters or metrics used will now be considered.

A first metric for consideration is Acute:Chronic Workload Ratio (ACWR). ACWR is the ratio of the distance run in the previous 7 days (acute workload) to the average workload encountered during the previous 28 days (chronic workload). It is a well-recognised metric in its own right and it is in common usage in academic studies and professional sports. Awareness of this metric is also increasing amongst enthusiastic amateur athletes.

Evidence of the usefulness of this measurement in indicating a healthiness and/or sustainability of a subject's running behaviour may be found in: "The training-injury paradox: should athletes be training smarter and harder", Gabbett T J (2016), British Journal of Sports Medicine. 50, 273-280 (suggesting that training load ratios between 0.80-1.30 exhibit reduced injury rate); "Spikes in acute workload are associated with increased injury risk in elite cricket fast bowlers", Hulin B T (2014), British Journal of Sports Medicine. 48, 708-712 (from which it is understood that large increases in acute workload are associated with increased injury risk); and "Individual and combined effects of acute and chronic running loads on injury risk in elite Australian footballers", Murray N B et al (2017), Scandinavian Journal of Medicine and Science in Sports. 27, 990-998 (identifying that sharp increases in running workload increase the likelihood of injury in both the week the workload is performed and the subsequent week).

An example of its calculation is as follows. A user runs 10 km in the current week. The user has run a total of 50 km in the previous 28 days. Then, Acute workload=10 km; Chronic workload=12.5 km (50/4); and ACWR=0.8 (10/12.5).

A second metric that may be used is pronation. As discussed above, pronation is an umbrella term used to describe a classification for the motion of the foot as it makes initial contact with the ground (first 50% of each stance period) during a step whilst the user is running. Three types of Pronation are commonly recognised: "Neutral pronation" (NP) defined as a ground contact where downward force through the medial and lateral regions of the foot is in approximate equilibrium; "Over Pronation" (OP) defined as a ground contact where downward force through the medial region of the foot is greater than that exerted through the lateral region (in effect, the foot is rolled excessively through contact with the ground); and "Under Pronation" (UP) defined as a ground contact where force through the lateral region of the foot is greater than that exerted through the medial region (in effect the user strikes the ground using disproportionate force through the lateral region, that is outside, of the foot, not absorbing adequate force through the medial region. A method for determining pronation has been discussed above For the purposes of Running Health, only NP is assessed. This behaviour is associated with a reduced injury risk and both of the other pronation behaviours may be associated with elevated injury risk. The higher the incidence of NP measured as a percentage of all steps taken during a run, the higher the value assigned to this factor. NP is measured independently for the left and right feet.

Evidence of the usefulness of this measurement in indicating a healthiness and/or sustainability of a subject's running behaviour may be found in: "Medial shoe-ground pressure and specific running injuries: A 1-year prospective cohort study", Brund R B K et al (2017), Journal of Science and Medicine in Sport, http://dx.doi.org/10.1016/j.jsams.2017.04.001 (indicating that a higher incidence of lower leg injuries with more medial foot loading); and "Biomechanical predictors of retrospective tibial stress fractures in runners", Pohl M B et al (2008), Journal of Biomechanics, 41, 1160-1165 (in which it is suggested that greater values of peak rearfoot eversion, which is a component of over-pronation, were associated with a greater risk of tibial stress fracture in female runners).

Cadence is a third possible metric. Cadence is a common running metric defined as the number of steps per minute (spm) the user takes during running. For the purposes of Running Health, a cadence measurement is taken at regular intervals (for example, every 400 ms) during the run. Following the run, these cadence values are averaged together to produce an average cadence value for the run. Higher average cadence is more desirable than lower average cadence, so the scale used to assign a value to this factor reflects this.

Evidence of the usefulness of this measurement in indicating a healthiness and/or sustainability of a subject's running behaviour may be found in: "Hip muscle loads during running at various step rates", Lenhart R et al (2014), Journal of Orthopaedic & Sports Physical Therapy, 44, 766-774 (suggesting that less muscle work is associated with higher cadence); "Effects of step rate manipulation on joint mechanics during running", Heiderscheit B C et al (2011), Medicine & Science in Sports & Exercise, 43, 296-302 (which links higher cadence with less joint loading); and "The effects of running cadence manipulation on plantar loading in healthy runners", Wellenkotter J et al (2014) (associating less foot pressures and/or impact forces with higher cadence).

As previously indicated, asymmetry is a further metric which can be considered. In particular, asymmetry of one or more of: cadence; pronation; footstrike; and step length can be assessed. Asymmetry for running purposes may be defined as the degree of difference between the behaviour of the user's left and right legs or feet. It is generally assessed across a number of running form factors, and it is expressed as a percentage difference in each case.

Evidence of the usefulness of asymmetry in indicating a healthiness and/or sustainability of a subject's running behaviour may be found in: "Contralateral leg deficits in kinetic and kinematic variables during running in Australian rules football players with previous hamstring injuries", Brughelli M et al (2010), Journal of Strength and Conditioning Research, 24, 2539-2544 (providing some evidence of left-right differences with injury history); http://running-.competitor.com/2016/01/injury-prevention/symmetry-and-running_144007 (indicating that symmetry is a component of good running behaviour); and "Kinetic asymmetry in female runners with and without retrospective tibial stress fractures", Zifchock (2006) (from which it is understood that asymmetry in loading may associate with injuries on the same side).

For cadence asymmetry, the difference between the spm count between the left and right legs is determined. This may be calculated at frequent intervals throughout the run and then averaged across the duration of the run to produce a single value. Pronation asymmetry is determined based on a difference in the ratio between downward force exerted through the medial and lateral regions of the foot, for the left and right foot. This can be calculated at frequent intervals throughout the run and then averaged across the duration of the run to produce a single value.

As identified above, footstrike is a metric that classifies initial ground contact on each step during running into one of three categories: forefoot strike (FFS, a ground contact where the front of the foot strikes the ground first); mid-foot strike (MFS, a ground contact where the mid-portion of the foot strikes the ground first); and rear-foot strike (RFS, a ground contact where the rear of the foot strikes the ground first). For the purposes of determining asymmetry, steps during a run are grouped into pairs, each pair comprising a left and a right step. If a pair contains the same kind of footstrike (for example, two mid-foot strikes) then it is classed as symmetrical. Otherwise, it is classed as asymmetrical. The number of asymmetrical step pairs across the entire run can be calculated at the end of the run, for instance as a percentage of the total number of steps taken.

Step length asymmetry may be determined from step length. Step length is a metric which reports the distance covered by a step, defined as the distance over ground covered in the running direction from one foot ground contact to the next ground contact by the other foot. Step length asymmetry may then be defined as a measure of the difference in step length between steps made by the left and right legs. This can be expressed as a percentage, recorded on a per-step basis and averaged across the duration of the run to produce a single value.

Figure 3:
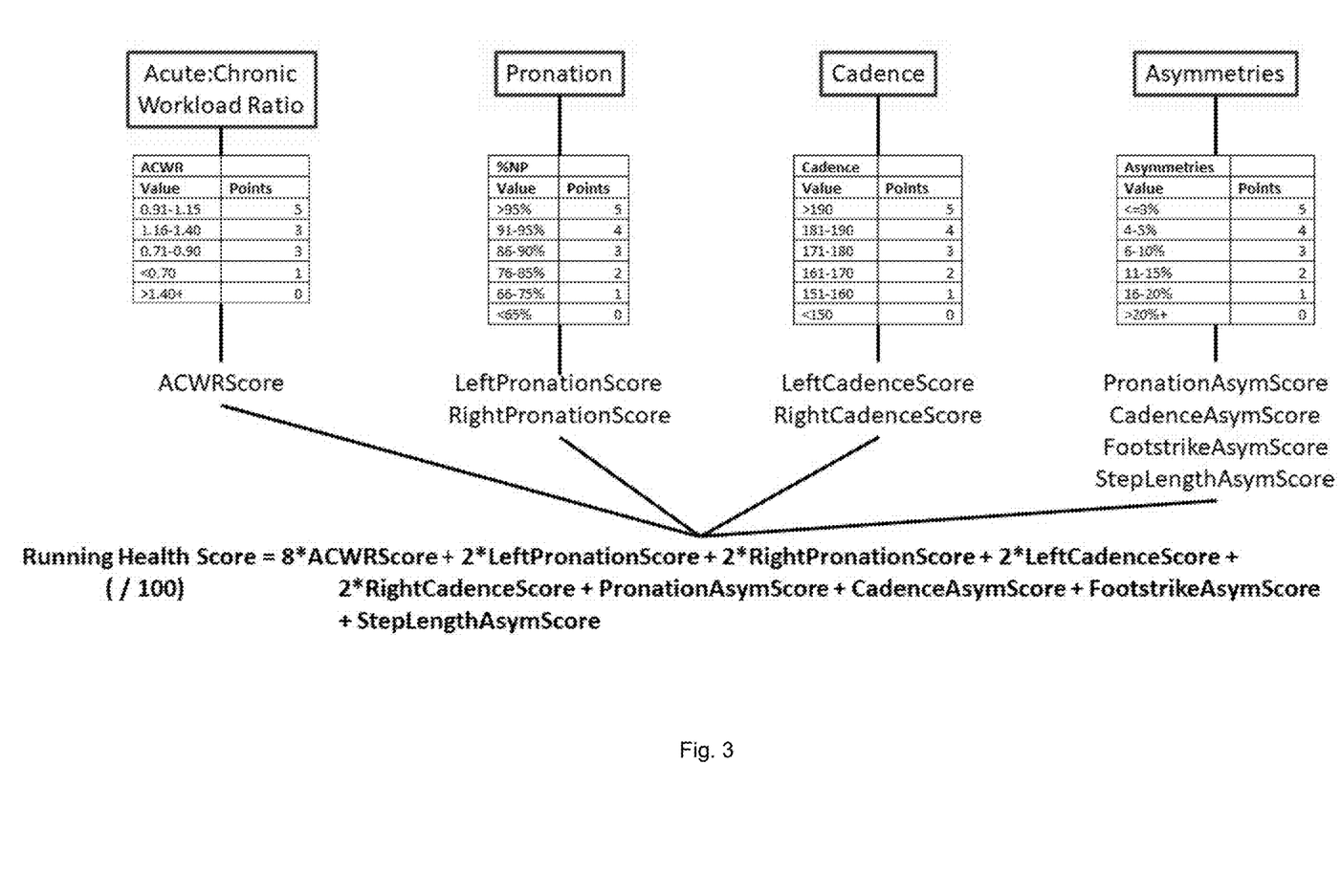
FIG. 3 depicts a specific approach in accordance with FIG. 2.

With reference to FIG. 3, there is depicted a specific approach for calculating the overall metric, which will be discussed below. As indicated previously, each of the metrics is then classified into categories. Examples of a score or points allocated to each category is given in the following tables.

| ACWR | |
|---|---|
| Value | Points |
| 0.91-1.15 | 5 |
| 1.16-1.40 | 3 |
| 0.71-0.90 | 3 |
| <0.70 | 1 |
| >1.40+ | 0 |

| % NP | |
|---|---|
| Value | Points |
| >95% | 5 |
| 91-95% | 4 |
| 86-90% | 3 |
| 76-85% | 2 |
| 66-75% | 1 |
| <65% | 0 |

| Cadence | |
|---|---|
| Value | Points |
| >190 | 5 |
| 181-190 | 4 |
| 171-180 | 3 |
| 161-170 | 2 |
| 151-160 | 1 |
| <150 | 0 |

| Asymmetries | |
|---|---|
| Value | Points |
| <=3% | 5 |
| 4-5% | 4 |
| 6-10% | 3 |
| 11-15% | 2 |
| 16-20% | 1 |
| >20%+ | 0 |

The value assigned is then weighted using a coefficient determined by the factor in question and this final value is passed into the equation to determine Running Health. In other words, the score or points are combined to give an overall Running Health metric based on a weighted sum of the factor scores. This is calculated using the weights given in the following table.

| Variable | Weighting |
|---|---|
| Left Cadence | 2 |
| Right Cadence | 2 |
| Left % NP | 2 |

-continued

| Variable | Weighting |
| --- | --- |
| Right % NP | 2 |
| Cadence Asymmetry | 1 |
| Pronation Asymmetry | 1 |
| Step Length Asymmetry | 1 |
| Footstrike Asymmetry | 1 |
| ACWR | 8 |

The weighting of metrics within the Running health calculation is based on a judgement of the strength of evidence available for the association between the individual metric and/or combined measure. It will be seen that the weight applied to ACWR is higher (twice as much as) other factors. This is in view of the strength of evidence for this factor being stronger and/or more consistent than for other factors.

Returning to the generalised description of this aspect noted above, the following optional features may be considered.

For example, a measure of acute to chronic workload ratio for the subject may be determined. Then, the metric characterising the health of a subject's running behaviour may be further based on the determined measure of acute to chronic workload ratio. For example, the measure of acute to chronic workload ratio may be compared with at least one workload threshold. Then, the measure of acute to chronic workload ratio is advantageously classified based on the step of comparing. Beneficially, the classification is a number.

The metric characterising the health of a subject's running behaviour may then be based on a combination of the identified plurality of classifications for respective asymmetry levels and the classification for the measure of acute to chronic workload ratio, for example as a linear combination, arithmetic combination, sum or weighted sum. In particular, the metric characterising the health of a subject's running behaviour is preferably based on a weighted sum of the plurality of classifications for respective asymmetry levels and the classification for the measure of acute to chronic workload ratio. Then, the weight for the classification for the measure of acute to chronic workload ratio is advantageously higher than the weight for each of the plurality of classifications for respective asymmetry levels.

Additionally or alternatively, a cadence metric may be measured at the processor, based on a combination of pressure sensor measurement signals received from the first and/or second foot-based sensor device, in respect of the first and/or second foot of the subject. The measured cadence metric for the first foot may be compared with a first foot cadence threshold and/or the measured cadence metric for the second foot may be compared with a second foot cadence threshold (which is typically the same as the first foot cadence threshold). The measured cadence metric for the first foot and/or the measured cadence metric for the second foot are classified based on the step of comparing. There may be multiple first foot cadence thresholds and/or multiple second foot cadence thresholds in order to provide more than two classifications. Advantageously, each classification is a number. Then, the metric characterising the health of a subject's running behaviour is based on at least one asymmetry level or a combination of the identified plurality of classifications for respective asymmetry levels and the classification for the measured cadence metric, for example as a linear combination, arithmetic combination, sum or weighted sum.

Additionally or alternatively, a pronation metric may be measured at the processor based on a combination of pressure sensor measurement signals received from the first and/or second foot-based sensor device, in respect of the first and/or second foot of the subject. The measured pronation metric for the first foot may be compared with a first foot pronation threshold and/or the measured pronation metric for the second foot may be compared with a second foot pronation threshold (which is typically the same as the first foot pronation threshold). The measured pronation metric for the first foot and/or the measured pronation metric for the second foot are classified based on the step of comparing. There may be multiple first foot pronation thresholds and/or multiple second foot pronation thresholds in order to provide more than two classifications. Advantageously, each classification is a number. Then, the metric characterising the health of a subject's running behaviour is based on at least one asymmetry level or a combination of the identified plurality of classifications for respective asymmetry levels and the classification for the measured pronation metric, for example as a linear combination, arithmetic combination, sum or weighted sum. The pronation metric for the first foot and/or pronation metric for the second foot may be determined in accordance with any of the methods indicated herein for determining pronation.

Field Calibration

As noted above, foot-based or shoe-based pressure measurements may be used in various ways to determine metrics. It is desirable that the pressure sensors, particularly Force Sensitive Resistors (FSR), which can record pressure distribution patterns occurring across the bottom surface of the foot during running ground contacts, provide useful outputs. For example, over a period of time, the output characteristics of each FSR (such as the 16 in each insole, as shown in FIG. 1) may change. This may affect the magnitude of response and/or allow a drift from the original baseline (zero) levels.

Calibration is intended to mitigate and correct for any change in the sensor characteristics, to ensure that the foot-based metrics give sensible outputs, be more robust and have longer lifetime. These calibrations are advantageously performed whilst the system is in use, so as not to require a return to supplier or factory.

To achieve this, it has been recognised that measurements taken during normal operation of the sensor device (typically an insole or embedded into a shoe) can be used for calibration (so-called, field calibration). By identifying minimum values for the sensor outputs during suitable conditions and using these to set calibration or correction constants dynamically during use, the accuracy and usefulness of the sensor outputs can be maintained for longer. This can be done by electronic processing of the output signals, using hardware and/or software.

In general terms, there may be considered a method for calibrating a measurement from a shoe-based sensor device. The device is used for measuring pressure at one or more parts of a shoe sole and provides a pressure sensor measurement signal indicating the measured pressure. The method is performed at a processor that receives the pressure sensor measurement signal. A minimum value for the pressure sensor measurement signal is determined. Beneficially, the determined minimum value is stored as a correction constant in a data memory associated with the processor. Then, a value for the pressure sensor measurement signal received subsequent to the step of storing is corrected by the stored correction constant. This approach is preferably used for multiple pressure sensor measurement signal, each indicating a respective measured pressure (for instance, from the same device, such as an insole or shoe). In particular, each measured pressure is for a different part of the shoe sole. Then, a minimum value for each pressure sensor measurement signal is determined and each determined minimum value is stored as a respective correction constant in the data memory. A value for each pressure sensor measurement signal received subsequent to the step of storing is corrected by the respective stored correction constant.

Whether one pressure sensor measurement signal or multiple pressure sensor measurement signals are corrected, each minimum value is preferably determined from a plurality of samples of the respective pressure sensor measurement signal taken over a time duration. The time duration is advantageously selected to be during normal operation of the shoe-based sensor device, which may include a time duration when the device is being used (for example, the shoe or foot is being moved) and/or a time when the device is awaiting use (for instance, sitting stationary in a shoe without any load being applied). In some embodiments, the time duration may be selected to occur at regular intervals. Further details of this generalised description will be discussed below, but more specific description of possible implementations will firstly be provided below.

Two specific calibration methods have been considered: "in run", allowing dynamic calibration during movement; and "zero load", in which a non-usage condition is identified for the device, allowing calibration measurements to be taken. These will be presented individually below.

"In Run" calibration involves "baselining" (resetting to zero) each of the sensor (FSR) outputs, by sampling the initial input data from each sensor and performing a procedure that retains the minimum value. This minimum value is used as a correction constant from which to subtract from all subsequent raw data points. Beneficially, this procedure may extend the operational life of a pressure sensor-based insole or shoe, can occur automatically in the background and does not require any action on the part of the user.

Figure 4:
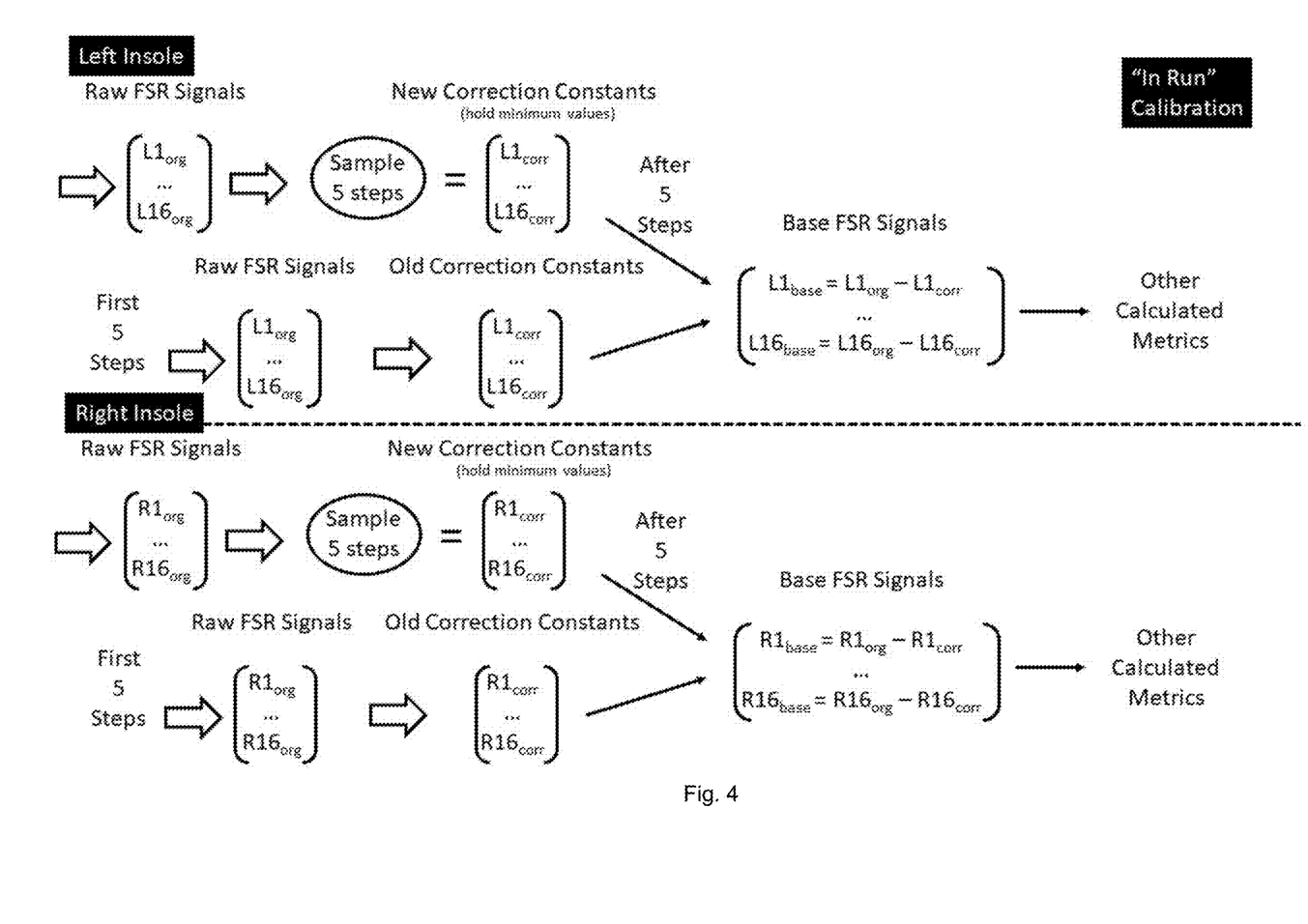
FIG. 4 schematically shows a first algorithm for field calibration of a pressure sensor for taking foot-based measurements.

Referring to FIG. 4, there is schematically shown an algorithm for field calibration of a pressure sensor for taking foot-based measurements, in accordance with this approach. The algorithm of the procedure will be described below.

Arrays of original FSR signals are continuously collected from left and right insoles ($L1_{org}$ ... $L16_{org}$ and $R1_{org}$ ... $R16_{org}$). Previously stored values for baselining constants are available ($L1_{corr}$ ... $L16_{corr}$ and $R1_{corr}$ ... $R16_{corr}$), with a factory default of 0.0. For each FSR sample (taken at a rate of 1000 Hz): arrays of baselined FSR signals are created ($L1_{base}$ ... $L16_{base}$ and $R1_{base}$ ... $R16_{base}$), for example $L1_{base}=L1_{org}-L1_{corr}$. In this way, each 'original' data point for the 32 FSRs (16 for each of the left and right insoles) has a corresponding 'base' data point (sampled at 1000 Hz).

For each run session, the first 5 steps worth of data are sampled and the minimum value observed from the 'original' FSR data streams is held. The minimum values are stored as the new baselining constant ($L1_{corr}$, ... $L16_{corr}$ and $R1_{corr}$ ... $R16_{corr}$). From the time point that more than 5 steps have been taken in each run session, the 'base' arrays are determined based on the newly updated correction factors. The 'base' arrays are used in all downstream calculation of metrics.

Returning to the generalised description discussed above, a time period in which the shoe is undergoing movement may be identified, based on the at least one pressure sensor measurement signal. Then, the plurality of samples of the pressure sensor measurement signal (or signals) are advantageously collected for determining each minimum value, over a time duration within the identified time period. For instance, a time period in which the shoe takes a predetermined number of steps may be identified. The predetermined number of steps may be at least one, is preferably at least two, more preferably at least three, four, five, six, seven, eight, nine or ten. The predetermined number of steps may be no higher than five, ten or fifteen in some embodiments. The predetermined number of steps may be defined based on the first steps in which a specific type of movement (for example walking or running) is identified. The steps of identifying and collecting are beneficially repeated at (regular) time intervals.

The baselining constants may be used as a basis to adjust the magnitude threshold values used to detect steps (for instance using a whole foot), rearfoot contact, and forefoot contact. This effectively acknowledges that the baselining procedure may reduce the maximum signal that can be reached in each zone, by adjusting (lowering) the threshold value.

Thus, when using the technique of FIG. 4 or similar, the procedure or algorithm for determining footstrike may be adapted accordingly. This is because, when an individual FSR has undergone the baselining procedure, this effectively reduces the dynamic range of that sensor, as it may not go through the same magnitude fluctuations. This means that the thresholds for detecting whole foot, rearfoot and forefoot contact are desirably adjusted to account for the influence of reduced dynamic range of any baselined FSRs in the respective zones. The procedure that may be used for a specific foot is described as follows. The procedure may be repeated for each foot individually.

Firstly, the newly stored minimum values for each FSR are summed for each zone: rearfoot (for example, FSR1,2, 3,16); midfoot (for example, FSR5,6,8,11,13,14); and whole foot (all sensors or a predetermined different subset of sensors). Then, the proportion of full effective ADC range (52000 units per FSR) that is lost due to having re-baselined any FSR in that zone is calculated. This is determined by dividing the sum of the correction constants for sensors in that zone by the sum of the original effective ADC range (52000 units multiplied by number of FSRs making up the zone). The 'remaining' ADC range is the established as the original ADC range (100%) subtracted by the proportion of 'lost' ADC range. The 'remaining' proportion of ADC range is multiplied by the original zone threshold value (for instance, 40000 units as discussed above) to calculate the new threshold for that zone. The new threshold values are stored and used as the value which is to be exceeded on each occasion to detect steps, based on whole foot, rearfoot, or midfoot contact, respectively.

For similar reasons as for footstrike, the Pronation calculation may be adjusted to account for the fact that the 'medial' zone and 'lateral' zone may have had different amounts of baselining dependent on the state of the respective FSRs. This may therefore assist to preserve the integrity of the medial and/or lateral ratio calculation, by using "correction factors" for each zone following the in-run calibration. These may be used as an integral part of the pronation calculation.

Adjustments may hence be made to the pronation calculations discussed above to account for reduced dynamic range of FSRs. As with the footstrike calculations discussed above, when each individual FSR has undergone the baselining procedure, this may effectively reduce the dynamic range of that sensor, as it may not go through the same magnitude fluctuations). This may means that the ratio calculation between the "medial" zone and the "lateral"

zone, which is the basis of the pronation calculation discussed herein could be disrupted if the extent of baselining is different between these two zones.

To compensate for this, an additional correction may be implemented to mitigate the effect of different amounts of baselining between "medial" and "lateral" zones. The adjusted procedure for calculating pronation for a specific foot is detailed below. The procedure may be repeated for each foot individually.

Firstly, medial and/or lateral correction factors due to the baselining in-run calibration are calculated, for example at the end of the in-run calibration procedure. This the newly stored minimum values for each FSR are summed for each zone: "medial" (6 FSRs, for example FSR2,3,4,5,6,8 as suggested above); and "lateral" (6 FSRs, for example, FSR1,16,15,14,13,11 as suggested above). Separately for each of the "medial" and "lateral" zones, a respective "remaining dynamic range" is calculated. This is determined by taking original available effective range (for instance, 52000 units multiplied by number of FSRs making up the zone) subtracted by the sum of the baselining constants for the sensors in that zone. This procedure is similar to the approach taken with respect to footstrike above. Then, a "Medial Correction Factor" and a "Lateral Correction Factor" are calculated by dividing original available effective range for the respective zone by the remaining dynamic range for the respective zone. These correction factors are then stored for use in the pronation ratio calculation. In particular, the MedialPressure and/or LateralPressure values used in the calculation may be adjusted by the appropriate correction factor for the foot and zone, as discussed above.

In respect of footstrike and/or pronation calculation, the procedure discussed above may be viewed as an additional step occurring at the completion of the 'in-run calibration' to produce the "correction factors". These correction factors are advantageously integrated into an updated method for calculating the footstrike and/or pronation value for each step. The skilled person will recognise that other sensor-based measurements that may vary based on changes to the respective sensor's dynamic range, may be adjusted in a similar fashion by determining a "remaining dynamic range" for the sensor or group of sensors using the procedure as described above.

In general terms, this may be considered as: determining an overall dynamic range for a sensor or a group of sensors; determining a remaining dynamic range for the sensor or the group of sensors, based on the overall dynamic range and the respective stored correction constant for the sensor or the group of sensors; and adjusting a pressure threshold and/or pressure level (the pressure level being based on one or more of received pressure sensor measurement signals) for the sensor or the group of sensors based on the remaining dynamic range. For instance, the ratio of the remaining dynamic range to the overall dynamic range may be calculated. This may then be used as an adjustment factor (coefficient) for the pressure threshold and/or pressure level. Multiplication of the pressure threshold and/or pressure level by the adjustment factor may set a replacement pressure threshold and/or pressure level to be used in a method based on the pressure threshold and/or pressure level, for example as those discussed herein with reference to footstrike, pronation or other step-based metrics.

"Zero Load" calibration involves the user performing a standalone periodic collection of insole data to execute the baselining function. This would likely be prompted via a notification in an application used by the user to view data collected (for example in a smartphone or smart watch). During this procedure, the user is encouraged to activate the system whilst the insoles are located in their running shoes, but they are not wearing the shoes (to effect zero load).

The user is directed through a 'journey' (via the application), where the system collects data in this "zero load" mode and the correction constants are obtained as the average of each FSR output value in this state. These correction constants are then subtracted from all subsequent raw FSR data points. This calibration procedure could be prompted at periodic intervals. The calibration procedure typically involves user interaction (but not necessarily) and in that case, is visible to the user.

The benefits of executing this calibration procedure is that it can extend the operational life of a pressure sensor-based insole. It does require a user-initiated procedure to run, but could be adapted to alert the user to when would be an appropriate time to replace a pair of smart insoles.

Figure 5:
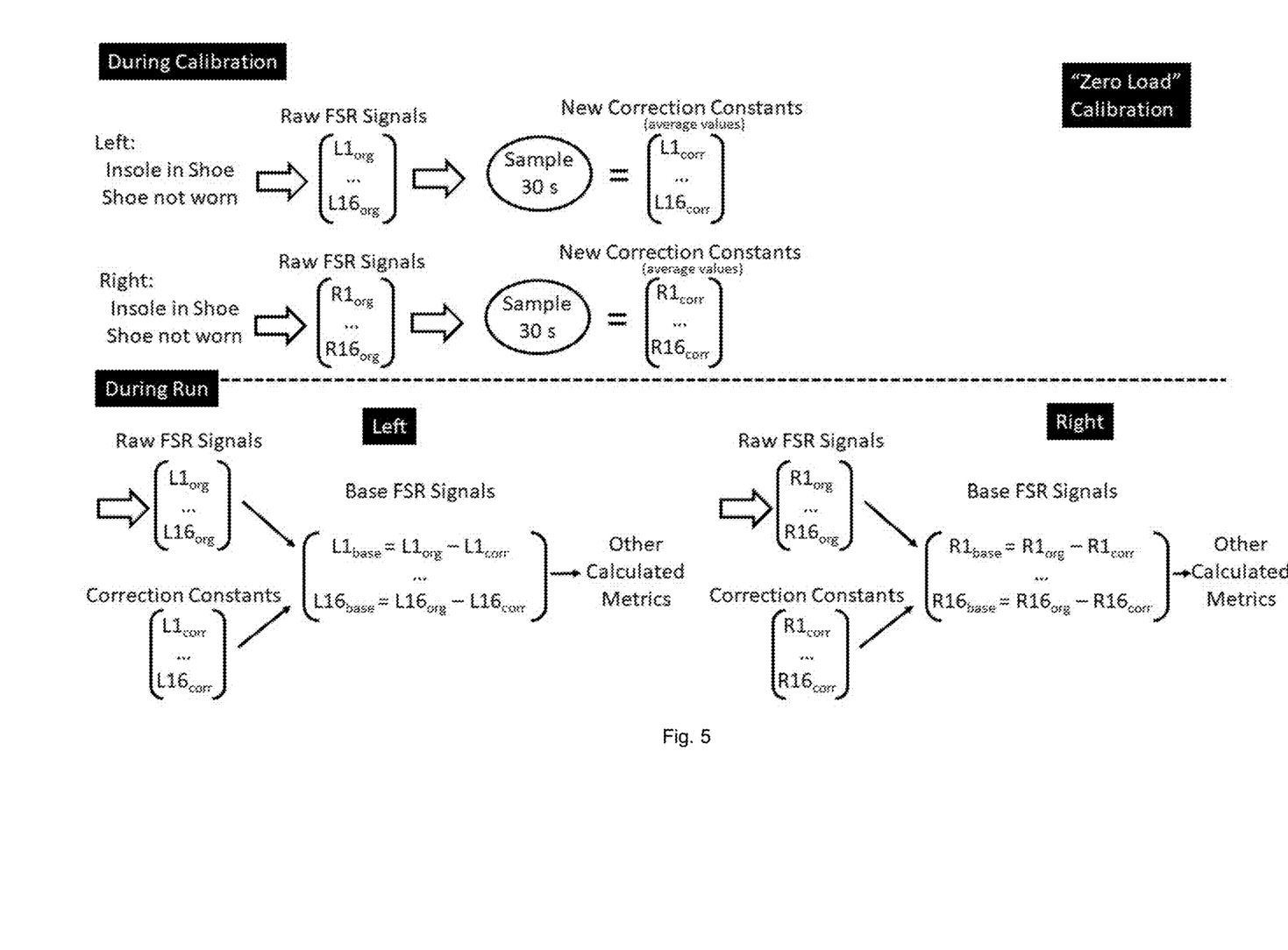
FIG. 5 schematically shows a second algorithm for field calibration of a pressure sensor for taking foot-based measurements.

Referring to FIG. 5, there is schematically shown an algorithm for field calibration of a pressure sensor for taking foot-based measurements, in accordance with this approach. The algorithm of the procedure will be described below.

During calibration, for each individual insole: a 30 second time period is defined, whilst insole is in shoe but not being worn ("zero-load") and sensor data is collected for this period. Then, for each individual FSR, a baselining "zero-load" value is determined by averaging the data collected over the time period and this is stores as the 'baselining constant'.

During running, for each individual FSR, raw data is recorded at a sampling rate (1000 Hz) and the relevant 'baselining constant' value is subtracted from each original FSR value and stored, such that for example, $L1_{base} = L1_{org} - L1_{corr}$. A new FSR 'base' data stream is thereby generated, in which the FSR output has been zeroed based on the zero-load value. The 'base' arrays are used in all downstream calculation of metrics.

With reference to the generalised description discussed above, it may be understood that a signal is received at the processor indicating that no load is being applied to the shoe. This signal may be user-generated, it may be determined by other sensors (such as an accelerometer, proximity sensor or other type of pressure sensor) or it may be generated within the processor by data analysis from the pressure sensors and/or other sensors. Then, the plurality of samples of the pressure sensor measurement signal (or signals) are advantageously collected for determining each minimum value. This beneficially occurs over a time duration having a start set in response to receiving the signal. The time duration preferably has a predetermined length, for example at least 20 seconds and/or no more than one minute and preferably around 30 seconds.

Using Heart Rate to Detect Changes in Fitness

A further aspect of the system may measure aerobic fitness. This is typically assessed by measuring maximum oxygen uptake. In a mixed group of runners, better aerobic fitness generally relates to better running performance. However, in a narrower demographic, maximum oxygen uptake does not necessarily dictate who will perform better.

A measure that has been used to distinguish between better and poorer running performance is "Running Economy". Running Economy is the understood as the rate of oxygen consumed at a given running speed. Lower usage of oxygen for a given speed is considered better running economy. However, measuring oxygen uptake in real-life situations is not practical (requiring heavy equipment or being otherwise invasive).

It has been recognised that oxygen uptake has a linear relationship with heart rate, particularly for submaximal steady-state exercise, such as long runs. Therefore, changes in heart rate output can be used as a surrogate for changes in oxygen uptake. From this, dynamic changes in running economy could be measured. For example, if for a given segment (a "split") of a run, the average heart rate of the subject appears lower than previous runs, whilst the pace of the split is maintained or improved, then the runner is improving running economy. Similarly, if for a given segment ("split") of a run, the average heart rate is being maintained in comparison with previous runs whilst the pace of the split is improved, then the runner is also improving running economy. In either sense, this is associated with getting fitter and improved performance.

A brief description of a technique for measuring running economy is now presented. The system can store run data against given routes and for given run types for each runner. The most reliable long-term comparisons would be made across the runs, which have been stored on the same route and with the same run type. This is because it can be assumed the intention of the runner has been similar. Runs can be segmented into "splits". Splits on level terrain provide the best opportunity for steady-state exercise (that is, no marked changes in heart rate or oxygen consumption due to inclines or declines). A comparison tool can search through the runner's run history for runs of same route and/or type. The tool can then selects one or more splits, which are considered to be run on level terrain (subject to some tolerance). For each attempt at the split, a comparison (mathematical regression) of average heart rate against attempt number allows the system to return an estimate of whether the user's running economy is improving. This comparison can further statistically control for any differences in split pace.

In general terms, there may be considered a method for measuring a change in aerobic fitness of a subject comprising: collecting first and second sets of heart rate measurements for a subject, each set of heart rate measurements being taken during respective movements of the subject (for example, walking and/or running) along the same geographical route (for example, determined using GNSS measurements, which may be taken simultaneously or substantively simultaneously with the heart rate measurements); determining a first heart rate statistic based on the first set of heart rate measurements and a second heart rate statistic based on the second set of heart rate measurements; and comparing the first heart rate statistic with the second heart rate statistic to provide a measurement of aerobic fitness change for the subject. The comparing may comprise a regression analysis. The first and second heart rate statistics may comprise or be based one or more of: averages; variances; standard deviations. Other statistical measurements could be made from the data.

Advantageously, the geographical route is selected to have a substantially level terrain (within a predetermined tolerance level). This may be achieved by selecting sets of heart rate measurements corresponding with such a geographical route from a larger set of heart data collected for a wider geographical route or by predetermining the geographical route and collecting data only for the predetermined geographical route.

Preferably, the time taken and/or movement speed are also collected for the movements. The step of comparing may further account and/or correct for the respective times taken and/or movement speeds.

Modifications, Variations and Combinations

Although specific embodiments have now been described, the skilled person will appreciate that various modifications and alternations are possible. For example, one or more of the number of pressure measurements, type of pressure sensors (for instance, switch-type arrangements, strain gauge devices or others, rather than FSRs), arrangement of pressure sensors, implementation of pressure sensors (which need not be an insole, but could be embedded in a shoe or sock, for example) could be varied in different permutations and combinations. Further variation may be made in respect of the parameters used in specific algorithms, as described herein.

All of the features disclosed herein may be combined in any combination, except combinations where at least some of such features and/or steps are mutually exclusive. Specific aspects as disclosed herein may be combined in different ways, some of which are expressly discussed above and others will be immediately apparent. In particular, features of the disclosure discussed or otherwise presented as preferred may be applicable to all aspects of the disclosure and may be used in any combination. Likewise, features described in non-essential combinations may be used separately (not in combination).

What is claimed is:

1. A method for calibrating a measurement from a shoe-based sensor device for measuring pressure at a part of a shoe sole and providing a pressure sensor measurement signal indicating the measured pressure, the method being performed at a processor that receives the pressure sensor measurement signal and comprising: determining a minimum value for the pressure sensor measurement signal and storing the determined minimum value as a correction constant in a data memory associated with the processor; and correcting a value for the pressure sensor measurement signal received subsequent to the step of storing, by the stored correction constant, such that the value of the pressure sensor measurement signal is altered in an amount corresponding to the correction constant.

2. The method of claim 1, wherein the processor receives a plurality of pressure sensor measurement signals, each pressure sensor measurement signal indicating the measured pressure at a different part of the shoe sole, the method comprising:
   determining, for each of the plurality of pressure sensor measurement signals, a respective minimum value and storing each determined minimum value as a respective correction constant in the data memory; and
   correcting a value for each of the pressure sensor measurement signals received subsequent to the step of storing, by the respective stored correction constant, such that the value for each pressure sensor measurement signal is altered in an amount corresponding to the respective correction constant corresponding to the pressure sensor measurement signal.

3. Method of claim 1, wherein the minimum value is determined from a plurality of samples of the pressure sensor measurement signal taken over a time duration.

4. The method of claim 3, further comprising:
   identifying, based on the pressure sensor measurement signal, a time period in which the shoe sole is undergoing movement; and
   collecting the plurality of samples of the pressure sensor measurement signal for determining the minimum value, over a time duration within the identified time period.

5. The method of claim 4, wherein the step of identifying comprises identifying a time period in which the shoe sole takes a predetermined number of steps, the predetermined number of steps being at least two.

6. The method of claim 5, wherein the predetermined number of steps is at least five.

7. The method of claim 4, wherein the steps of identifying and collecting are repeated at time intervals.

8. The method of claim 3, further comprising:
receiving a signal at the processor indicating that no load is being applied to the shoe sole; and
collecting the plurality of samples of the pressure sensor measurement signal for determining the minimum value, over a time duration having a start set in response to receiving the signal.

9. The method of claim 8, wherein the time duration has a predetermined length.

10. The method of claim 9, wherein the predetermined length is at least 20 seconds and no more than one minute.

11. A foot-based data metric system, comprising: a foot-based sensor device, the foot-based sensor device including a plurality of pressure sensors, each pressure sensor being configured to measure pressure at a different part of a foot and provide a pressure sensor measurement signal indicating the measured pressure; and a processor, configured to receive the pressure sensor measurement signal from each pressure sensor of the foot-based sensor device and to perform a method, the method comprising: determining a minimum value for each pressure sensor measurement signal and storing the determined minimum value as a correction constant in a data memory associated with the processor; and correcting a value for each respective pressure sensor measurement signal received subsequent to the step of storing, by the respective stored correction constant, such that the value for each pressure sensor measurement signal is altered in an amount corresponding to the respective correction constant.

12. The foot-based data metric system of claim 11, wherein the foot-based sensor device comprises a shoe insole, in which the plurality of pressure sensors are provided.

* * * * *